US010286169B2

(12) United States Patent
Heinonen et al.

(10) Patent No.: US 10,286,169 B2
(45) Date of Patent: May 14, 2019

(54) VENTILATOR SYSTEM AND METHOD FOR CONTROLLING THE SAME TO PROVIDE SPONTANEOUS BREATHING SUPPORT

(71) Applicant: General Electric Company, Schenectady, NY (US)

(72) Inventors: Erkki Paavo Heinonen, Helsinki (FI); Marc Wysocki, Buc (FR)

(73) Assignee: General Electric Company, Schenectady, NY (US)

( * ) Notice: Subject to any disclaimer, the term of this patent is extended or adjusted under 35 U.S.C. 154(b) by 288 days.

(21) Appl. No.: 15/423,340

(22) Filed: Feb. 2, 2017

(65) Prior Publication Data

US 2018/0214648 A1 Aug. 2, 2018

(51) Int. Cl.
*A61M 16/00* (2006.01)
*A61M 16/08* (2006.01)
(Continued)

(52) U.S. Cl.
CPC ...... *A61M 16/0081* (2014.02); *A61M 16/026* (2017.08); *A61M 16/0891* (2014.02);
(Continued)

(58) Field of Classification Search
CPC ............ A61N 16/0081; A61N 16/0891; A61N 16/026; A61N 16/107; A61N 16/22;
(Continued)

(56) References Cited

U.S. PATENT DOCUMENTS

2004/0249300 A1 12/2004 Miller
2007/0163590 A1 7/2007 Bassin
(Continued)

FOREIGN PATENT DOCUMENTS

| WO | 2008091789 A1 | 7/2008 |
|---|---|---|
| WO | 2009123981 A1 | 10/2009 |
| WO | 2013098717 A1 | 7/2013 |

OTHER PUBLICATIONS

Holk et al., "Continuous non-invasive monitoring of energy expenditure, oxygen consumption and alveolar ventilation during controlled ventilation: validation in an oxygen lung model", Acta Anaesthesiol Scand. 1996, 40; 530-537.
Laubscher et al., "An Adaptive Lung Ventilation Controller", IEEE 1994 (0018-9294).
Laubscher et al., "The automatic selection of ventilation parameters during the initial phase of mechanical ventilation", Intesive Care Med (1996) 22: 199-207.
(Continued)

*Primary Examiner* — Manuel A Mendez
(74) *Attorney, Agent, or Firm* — Andrus Intellectual Property Law, LLP

(57) ABSTRACT

A method of controlling a ventilator to provide spontaneous breathing support includes determining a target CO2 value, determining a support pressure, detecting a patient-generated spontaneous breath, and delivering ventilation gas to the patient based on the support pressure. A patient CO2 is then measured, along with measuring at least one of a patient breath rate and a breath volume. The patient CO2 is compared to the target CO2 value. The patient's respiratory drive is determined based on at least one of the patient breath rate and the breath volume. If elevated respiratory drive is detected, then the support pressure is adjusted accordingly. If elevated respiratory drive is not detected, then the target CO2 value is adjusted based on the measured patient CO2.

20 Claims, 4 Drawing Sheets

(51) Int. Cl.
*A61M 16/22* (2006.01)
*A61M 16/10* (2006.01)

(52) U.S. Cl.
CPC .......... *A61M 16/107* (2014.02); *A61M 16/22* (2013.01); *A61M 2016/0027* (2013.01); *A61M 2016/0039* (2013.01); *A61M 2016/0042* (2013.01); *A61M 2202/0208* (2013.01); *A61M 2205/502* (2013.01); *A61M 2230/202* (2013.01); *A61M 2230/432* (2013.01)

(58) Field of Classification Search
CPC .... A61N 2016/0027; A61N 2016/0039; A61N 2016/0042; A61N 2202/0208; A61N 16/0069; A61N 16/0051; A61N 16/024; A61N 16/205; A61N 16/00; A61N 16/0057; A61N 16/12; A61N 16/0003; A61N 2205/502; A61N 2230/202; A61N 2230/432
USPC .................................................. 128/204.23
See application file for complete search history.

(56) References Cited

U.S. PATENT DOCUMENTS

| | | |
|---|---|---|
| 2008/0236582 A1 | 10/2008 | Tehrani |
| 2010/0236555 A1 | 9/2010 | Jafari et al. |
| 2011/0301436 A1 | 12/2011 | Teixeira |
| 2012/0000470 A1 | 1/2012 | Hensley et al. |
| 2013/0047989 A1 | 2/2013 | Vandine et al. |
| 2015/0114395 A1 | 4/2015 | Heinonen et al. |

OTHER PUBLICATIONS

Westenskow et al., "A Microprocessor Based Feedback Controller for Mechanical Ventilation", Annals of Biomedical Engineering, vol. 10, pp. 35-48, 1982.

Drager, "Smart Ventilation Control (SVC)", 2016 Drägerwerk AG & Co. KGaA.

Drager, "Protective Ventilation in the OR", 2016 Drägerwerk AG & Co. KGaA.

VENTILATOR SYSTEM AND METHOD FOR CONTROLLING THE SAME TO PROVIDE SPONTANEOUS BREATHING SUPPORT

BACKGROUND

Ventilation support is needed when patient cannot meet the gas exchange demand with his own respiratory action. Such situations are typically during intensive care and surgical anesthesia. Typical reasons for inability to maintain the gas exchange demand may be sedation for therapeutic reasons including neural dampening and muscular relaxation and muscular weakening due to underlying disease. The ventilation support may be used to enhance carbon dioxide ($CO_2$) clearance and oxygen delivery to the patient. Further purpose of ventilation is delivery of inhalation anesthesia gas when ventilation is used during inhalation anesthesia.

Ventilation support divides into two categories: full mechanical ventilation and spontaneous breathing support, or pressure support. In mechanical ventilation, the ventilator dictates the breath rate and volume and is necessary where, for example, muscle relaxants are administered. By contrast, in spontaneous breathing support the patient maintains the respiratory rhythm and the ventilator is controlled to detect inspiration breaths. In spontaneous support ventilation, the ventilator adds inspiration pressure as a response to patient generated spontaneous breath.

Support of patient generated spontaneous breathing with added ventilation pressure is preferred ventilation on intensive care and also increasingly during anesthesia whenever the surgery does not require complete relaxation. The rationale for its use is to maintain patient's muscular activity and ease the weaning from ventilation.

In presently-available systems for spontaneous breathing support, the clinician controls the amount of ventilation to maintain appropriate subject's $CO_2$ concentration or partial pressure. This level can be determined by analysis of blood sample for arterial blood $CO_2$ partial pressure, $PaCO_2$. However, because this is a discrete measurement, end-expiratory gas $CO_2$ ($EtCO_2$) concentration is often used as surrogate for this. A typical $EtCO_2$ value is around 5%-6%, or 5-6 kPa, but in certain circumstances the optimum value may deviate from this.

Patient metabolic $CO_2$ production varies between subjects. This depends e.g. on subject size, age, gender, anxiety level, sedation, etc. Also some treatment actions vary the $CO_2$ level. To maintain the optimal subject $CO_2$ level the amount of ventilation must be adjusted to meet the $CO_2$ clearance demand. Furthermore, during mechanical ventilation this amount of ventilation must be divided between the breath rate and volume optimizing between minimal lung pressure and total amount of ventilation.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a method of controlling a ventilator to provide spontaneous breathing support includes determining a target $CO_2$ value, determining a support pressure, detecting a patient-generated spontaneous breath, and delivering ventilation gas to the patient based on the support pressure. A patient $CO_2$ is then measured, along with measuring at least one of a patient breath rate and a breath volume. The patient $CO_2$ is compared to the target $CO_2$ value. A difference between the patient $CO_2$ and the target $CO_2$ is determined, and the patient's breath rate and/or breath volume are analyzed to assess a change in the patient's respiratory drive. The target $CO_2$ value is adjusted based on the change in respiratory drive and the difference between the patient $CO_2$ and the target $CO_2$ value.

One embodiment of a ventilator system comprises a gas supply containing a breathing gas, a ventilator circuit that outputs the breathing gas from the gas supply to the patient and receives expiration gas from the patient, and a gas analyzer that measures a $CO_2$ content in the expiration gas and determines a patient $CO_2$ value. A spontaneous breathing support module is executable to define a target $CO_2$ value for spontaneous breathing support ventilation, define a support pressure for spontaneous breathing support ventilation, detect a patient-generated spontaneous breath, and deliver a ventilation gas to the patient based on the support pressure. The spontaneous breathing support module is further executable to receive a patient $CO_2$ measured in the patient's expiration gas, and to measure at least one of a patient's breath rate and breath volume. The patient $CO_2$ is compared to the target $CO_2$ value to determine that the patient $CO_2$. At least one of the patient's breath rate and the breath volume are analyzed to assess a change in the patient's respiratory drive. The target $CO_2$ value is then adjusted based on the change in respiratory drive and a difference between the patient $CO_2$ and the target $CO_2$ value.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Figure 1:
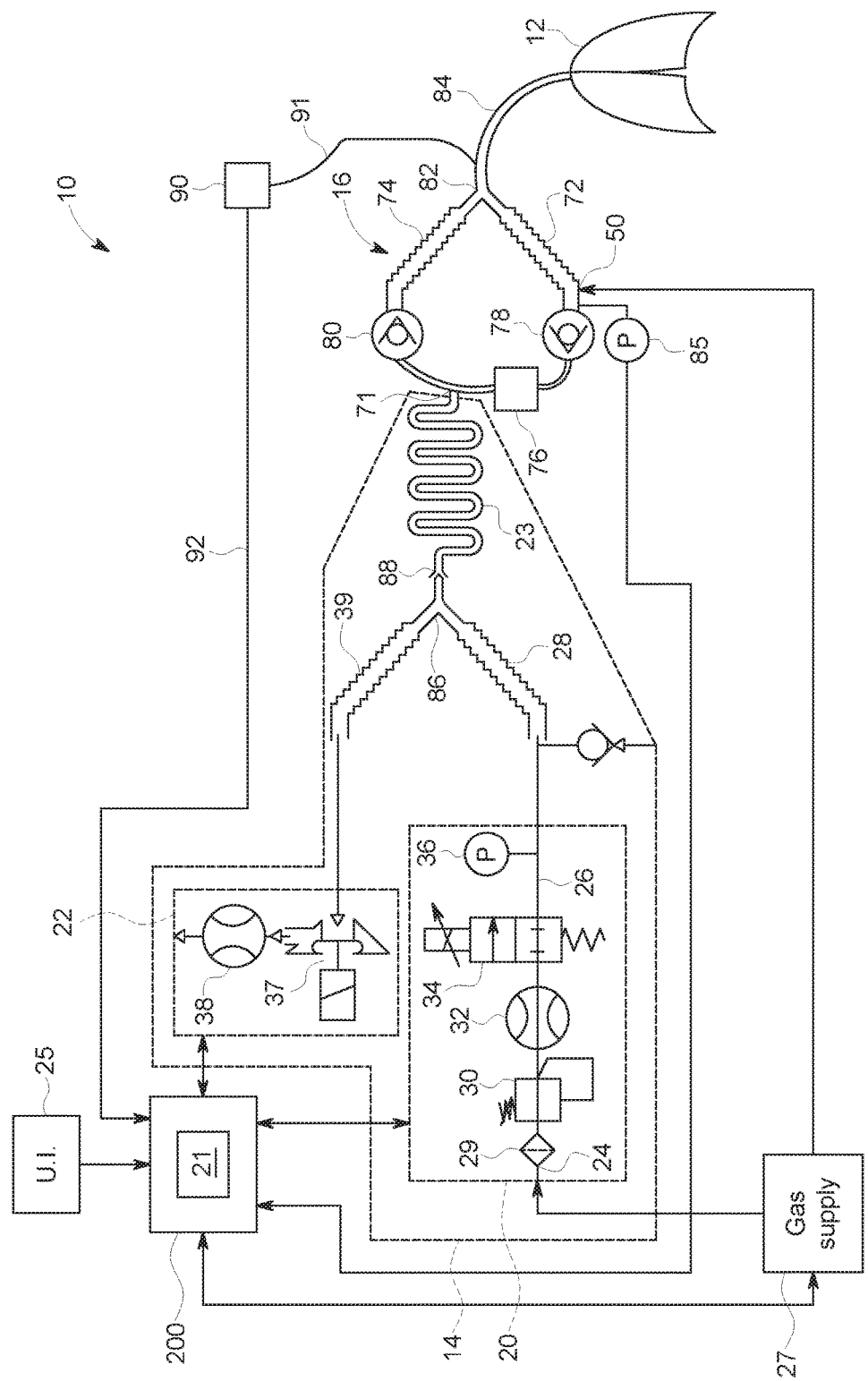
FIG. 1 is a schematic diagram of a ventilator system according to the present disclosure.

Patient respiratory center stimulation determines the spontaneous breath drive, breath frequency and/or intensity, and the main stimulant is the patient's $CO_2$ level. During spontaneous breathing support, the ventilator applies support pressure for ventilation at amount needed to maintain this $CO_2$ level. A central functionality of the patient's control system is the increase of respiratory center response with increasing patient respiratory stimulus. A support pressure that is too low will cause more $CO_2$ accumulation into body, thereby increasing the stimulus. This increases strength of respiratory center response, with the aim of enhanced ventilation and $CO_2$ clearance. Under most conditions, the stimulus and resulting clearance converge, providing balance between stimulus and response strength.

Control of ventilation amount to meet with the patient metabolic demand is important. In spontaneous breathing support ventilation, too high of a support pressure increases CO2 clearance and reduces body CO2 level, which dampens the respiratory center stimulus and strength of respiration response. This can result in prolonged weaning from ventilation. Too low of a support pressure causes a high respiratory center stimulus and such a strong response may lead to patient fatigue. Moreover, appropriate CO2 level is especially important in some disease states. As an example, for a neurosurgical patient, too high of a CO2 level increases brain blood circulation resulting in elevated intracranial pressure, a situation that may be disastrous to the patient. Conversely, too low of a CO2 level reduces brain circulation and may result as disastrous brain hypoxemia.

In view of the forgoing challenges and problems recognized by the inventors, they recognized a need for improved spontaneous breathing support that automatically varies the ventilation as a response to variations in patient conditions, adapting the amount of support pressure provided based on the CO2 stimulus and the patient's response. This support pressure determines the total amount of ventilation. However, difficulty lays in determining the amount of support pressure. The optimum CO2 level varies between individual patients and is influenced by a host of different factors. For example, the CO2 level required for spontaneous triggering, and consequently optimum the support pressure, depends on the level of sedative medication and patient metabolism, which both vary during the course of ventilation. Too high of a support pressure reduces body CO2 level, which dampens the patient's spontaneous activity. Too low of a support pressure increases the CO2 level increasing the spontaneous respiration drive strength resulting to fatigue if patient cannot cope with this.

During spontaneous ventilation support the CO2 target needs to correlate with the patient status to sustain spontaneous activity and avoid patient fatigue. Thus the control of support pressure developed and disclosed herein by the inventor adapts to the patient's respiratory center response, or drive. Namely, the pressure support controller receives information of the strength of respiratory drive using the resulting breath activity, which may include breath rate and/or breath volume. Information regarding the patient's CO2 level causing the respiratory center stimulus may be, for example, the measured end-tidal CO2 (EtCO2) value measured in the expiratory gases in the breathing circuit. Alternatively or additionally, the patient's CO2 may be determined based on measurements or estimations of the patient's arterial blood CO2 level.

The pressure support controller regulates the magnitude of the inspiratory support pressure supplied by the ventilator with the goal of reaching and maintaining a target EtCO2. As discussed above, the EtCO2 target value that would be optimum for the patient respiratory center stimulation is both unknown and variable in time. Accordingly, the method and system disclosed herein determine an optimal EtCO2 target, adapted based on the patient's spontaneous respiratory activity, or respiratory drive, including breath rate and breath volume (e.g., tidal volume). For this purpose, the measured respiratory drive value(s) is compared with respective threshold or target value—e.g. a target breath rate and/or target patient compliance (calculated based on breath volume, as is described in more detail below). A measured value exceeding the target indicates elevated respiratory drive and patient discomfort, while a value below the target indicates insufficient respiratory stimulus. These targets may be variable in time and determined based on the patient's condition, such as based on breath rate and breath volume values measured from the patient over time.

Accordingly, the patient determines the optimum target values, including target CO2, target breath rate, and/or target compliance value. Doing so avoids situation where ventilation support control works against the patient comfort level that the patient's respiratory center is aiming towards. For example, a target CO2 above the patient's comfort zone increases the patient's respiratory stimulus and respective breath response—e.g., causing the patient to increase their breath rate and/or the breath volume in order to decrease the patient's CO2 level. If the ventilator pressure support controller is aiming for a CO2 target higher than the patient's comfort level, the controller's reaction is to reduce support pressure to raise the CO2 level. This results in further increasing respiratory drive, thus causing further pressure support reduction. This vicious cycle leads to patient fatigue with undesired consequences. Likewise, excessive respiratory center dampening endangers a patient if the target CO2 for the ventilator pressure support controller is too low, below the patient's comfort level, which can reduce the patient's respiratory drive too much for maintaining the spontaneous activity.

FIG. 1 provides one embodiment of a ventilator system 10 for providing an inspiration gas to the subject 12 utilizing a re-breathing system. The ventilator system 10 comprises a machine ventilator circuit 14 for assisting breathing functions of the subject, a breathing circuit 16 for connecting lungs of the subject and the machine ventilator circuit 14 to exchange the gas in the lungs, and a spontaneous breathing support module 21 for controlling an operation of the ventilator system 10. The ventilator system 10 shown in FIG. 1 may also comprise a user interface 25 for entering any information needed while ventilating the subject and a gas supply 27 for supplying a fresh gas for the subject breathing.

The machine ventilator circuit 14 generally comprises an inspiration delivery unit 20 for delivering the gas such as drive gas needed to enable an inspiration of the subject, an expiration circuit 22 for controlling a discharge of the expiration gas and a reciprocating unit 23 such as a well-known bellows and bottle combination, where the bellows are arranged within the bottle, or a long gas flow channel as shown in FIG. 1 for compressing the gas under a control of the drive gas pressure towards lungs of the subject to facilitate the inspiration. Both the inspiration delivery unit 20 and the expiration circuit 22 are controlled by the spontaneous breathing support module 21.

As illustrated in FIG. 1, the inspiration delivery unit 20 comprises a compressed gas interface 24 connected to a compressed gas supply 27. The compressed gas can be either oxygen or air. Also a mechanism selecting the other if one gets de-pressurized can be applied (not shown). The inspiration delivery unit 20 comprises also a filter 29 for filtering impurities, a pressure regulator 30 for regulating a pressure of gases flowing from the gas interface, a flow sensor 32 for measuring a inspiration delivery flow from the gas interface and a flow control valve 34 for opening or closing the inspiration delivery flow. The flow sensor 32 and flow control valve 34 are each coupled to the spontaneous breathing support module 21 to control the inspiration delivery to the subject 12. Further the inspiration delivery unit 20 may comprise a pressure sensor 36 for measuring the gas pressure flowing along the conduit 26 and an inspiration branch 28 towards the reciprocating unit 23. Thereby, the breath volume can be determined based on the gas flow and pressure. In other embodiments, the spontaneous breathing support module 21 may be configured and utilized in connection with an intensive care unit (ICU) ventilator where the breathing circuit 16 is eliminated and the gas is delivered directly to the patient from connection point 88. In such an embodiment, two distinct inspiration control modules may be provided, one for controlling air delivery and the other for controlling O2 delivery to the patient.

The expiration circuit 22 comprises an expiration valve 37 for discharging the expiration gas and a flow sensor 38, which is optional, for measuring the flow discharged through the expiration valve 37. The expiration circuit is in flow connection along an expiration branch 39 with the reciprocating unit 23.

The gas supply 27 may also supply fresh breathing gas to the fresh gas outlet 50 in the breathing circuit. The gas supply 27 may include any number of one or more tanks or vessels containing gasses, which may be compressed gasses, to be delivered to the patient, such as oxygen, air, nitrous oxide, and/or volatile anesthesia agents. The gas supply 27 may further include a gas mixer to mix some or all of the various gasses being supplied to the patient, such as via the ventilator circuit 14 or before delivery to the fresh gas outlet 50, and may comprise any number of filters, a pressure regulators, an air flow sensors, and air flow control valves, etc. as is well known in the relevant art.

The breathing circuit 16, which is operably connected to the machine ventilator circuit 14 at a breathing circuit connection 71 and to the fresh gas outlet 50, comprises an inspiration limb 72 for an inspired gas, an expiration limb 74 for an exhaled gas, a carbon dioxide (CO2) remover 76 such as CO2 absorber to remove or absorb carbon dioxide from the exhaled gas coming from the subject 12, a first one-way valve 78 for an inspired gas to allow an inspiration through the inspiration limb 72, a second one-way valve 80 for an expired gas to allow an expiration through the expiration limb 74, a branching unit 82 such as a Y-piece having at least three limbs, one of them being for the inspired gas, a second one being for the expired gas and a third one being for both the inspired and expired gases and being connectable to by means of the patient limb 84 to the lungs of the subject 12. Also the breathing circuit may comprise a pressure sensor 85 for measuring a pressure of the breathing circuit 16.

During the inspiration phase of the machine ventilation the expiration circuit 22 of the machine ventilator circuit 14 closes the expiration valve 37 under the control of the spontaneous breathing support module 21. This guides the inspiration gas flow from the inspiration delivery unit 20 through the inspiration branch 28 of a gas branching connector 86 and through the connection 88 of the reciprocating unit 23 pushing the breathing gas out from the breathing circuit connection 71 to the breathing circuit 16. The inspiration gas delivery unit 20 controlled by the spontaneous breathing support module 21 delivers the gas flow either to reach the given gas volume or a pressure at breathing circuit measured. For this control the flow sensor 32 for measuring the inspiration flow and the pressure sensor 85 of the breathing circuit 16 are used.

At the end of the inspiration phase the breathing circuit 16 and the subject lungs are pressurized. For the expiration under the control of the spontaneous breathing support module 21 the inspiration delivery flow control valve 34 is closed stopping the inspiration delivery and the expiration valve 37 is opened to allow the gas release from the expiration branch 39 of the drive gas branching connector 86 and further through the connection 88 from the reciprocating unit 23. This allows the pressure release and breathing gas flow from breathing circuit 16 and the lungs of the subject 12 to the reciprocating unit 23. The breathing gas flows from the subject 12 through the patient limb 84, the branching unit 82, the expiration limb 74, the second one-way valve 80 for the expired gas and the breathing circuit connection 71 to the reciprocating unit 23. The pressure release is controlled for a desired expiration pressure such as a positive end expiration pressure (PEEP) target, which may be set using the user interface 25. For this control the spontaneous breathing support module 21 uses the breathing circuit pressure measured by the pressure sensor 85 and the expiration valve 37. The expiration gas flow may be measured using the flow sensor 38 located at the outlet the expiration valve 37 as shown in FIG. 1 or at any location on the expiration pathway from patient limb 84 to expiration valve 37.

FIG. 1 presents also a gas analyzer 90 to measure the concentrations of various gasses in the expiration gas from the patient, including the CO2 concentration. Such analyzer can be either side-stream type that suctions a sample gas stream through sampling line 91 for analysis or mainstream type where the analysis occurs in the gas stream in the patient limb 84. The analyzer communicates gas concentrations to the spontaneous breathing support module 21 through communication line 92. Gas analyzer 90 can be of any known type able to measure particular gas concentration. For CO2 infrared absorption is the most commonly used measurement principle.

Figure 2:
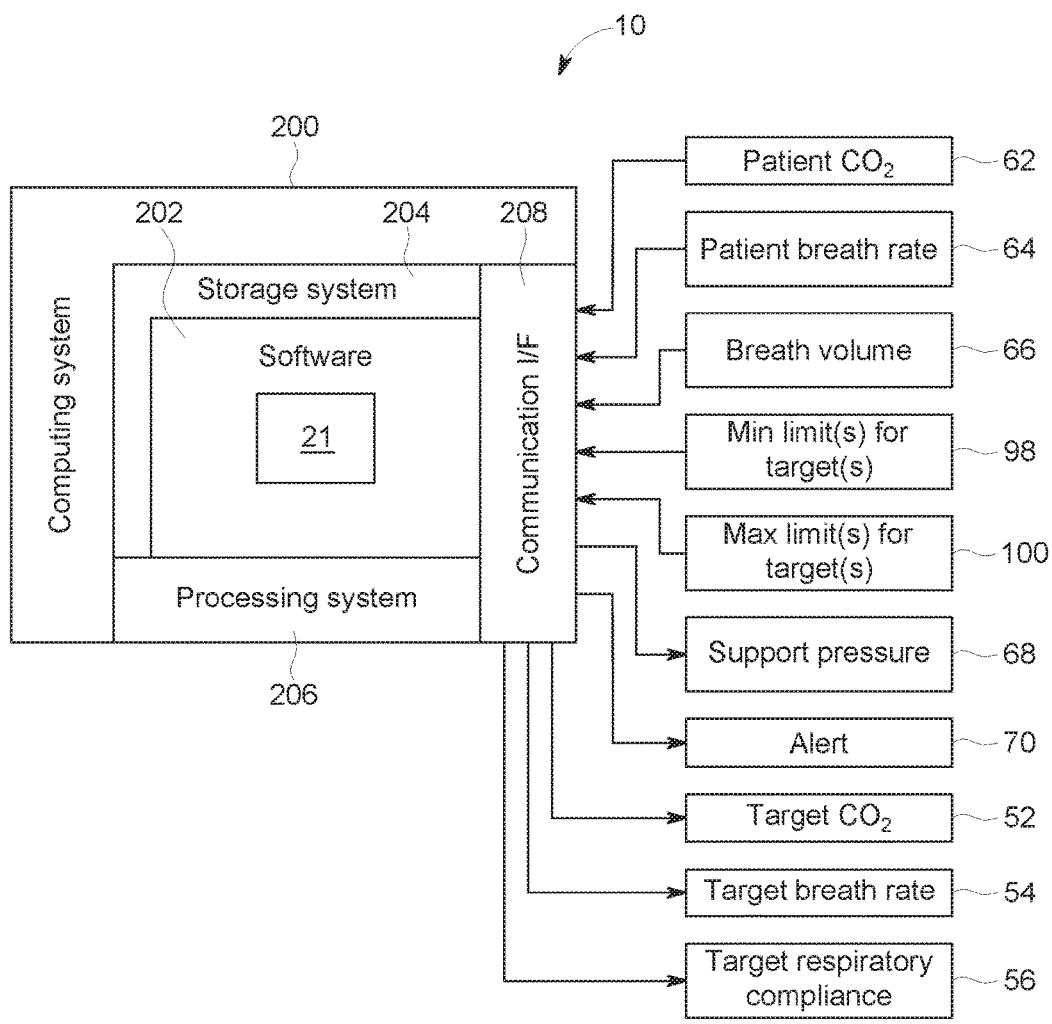
FIG. 2 is a schematic diagram of a computing system for a ventilator system of the present disclosure.

FIG. 2 provides a system diagram of an exemplary computing system 200 of an exemplary embodiment of the ventilation system 10 having a spontaneous breathing support module 21 executable to operate the ventilator circuit 14 to provide spontaneous breathing support ventilation to the patient. The computing system 200 includes a processing system 206, storage system 204, software 202, and a communication interface 208. The processing system 206 loads and executes software 202 from the storage system 204, including the spontaneous breathing support module 21, which is an application within the software 202. The spontaneous breathing support module 21 includes computer-readable instructions that, when executed by the computing system 200 (including the processing system 206), direct the processing system 206 to operate as described in herein in further detail, including to execute the steps to determine and provide an appropriate support pressure to assist the patient's respiration.

Although the computing system 200 as depicted in FIG. 2 includes one software 202 encapsulating one spontaneous breathing support module 21, it should be understood that one or more software elements having one or more modules may provide the same operation. Similarly, while description as provided herein refers to a computing system 200 and a processing system 206, it is to be recognized that implementations of such systems can be performed using one or more processors, which may be communicatively connected, and such implementations are considered to be within the scope of the description.

The processing system 206 includes the processor, which may be a microprocessor, a general purpose central processing unit, and application-specific processor, a microcontroller, or any other type of logic-based device. The processing system 206 may also include circuitry that retrieves and executes software 202 from storage system 204. Processing system 206 can be implemented within a single processing device but can also be distributed across multiple processing devices or sub-systems that cooperate in executing program instructions.

The storage system 204 can comprise any storage media, or group of storage media, readable by processing system 206, and capable of storing software 202. The storage system 204 can include volatile and non-volatile, removable and non-removable media implemented in any method or technology for storage of information, such as computer-readable instructions, data structures, program modules, or other data. Storage system 204 can be implemented as a single storage device but may also be implemented across multiple storage devices or sub-systems. Storage system 204 can further include additional elements, such a controller capable of communicating with the processing system 206.

Examples of storage media include random access memory, read only memory, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. Likewise, the storage media may be housed locally with the processing system 206, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 208 interfaces between the elements within the computing system 200 and other elements within the system 1, such as elements of the ventilator circuit 14, the gas supply 27, the breathing circuit 16, the gas analyzer 90, and the user interface 25. For example, the communication interface 208 receives the patient CO2, the patient breath rate 64, and the breath volume 66 delivered to the patient. The communication interface 208 communicates the support pressure 68 to the ventilator circuit 14 so that the appropriate ventilation support is provided to the patient. In certain embodiments, the communication interface may also communicate a control signal to the user interface 25 instructing generation of an alert 70, such as when the spontaneous breathing support module 21 determines that the patient's respiratory stimulus is too high or too low and/or when any of the target values determined for the patient reach a threshold value (such as the minimum or maximum values, as described herein). Additionally, the communication interface 208 may output the target values determined by the spontaneous breathing support module 21, including the target CO2 52, the target breath rate 54, and/or the target compliance value 56, for example to display one or more of the target values on a display of the user interface 25 and/or so that the target values can be stored in the patient's medical record. In certain embodiments, the communication interface 208 may also receive minimum limit(s) 98 and maximum limit(s) 100 for one or more of the targets, including the target CO2 52, the target breath rate 54, and the target compliance value 56. For example, the minimum limit(s) 98 and maximum limit(s) 100 may be inputted by a clinician via the user interface 25, or by some other means, and set an upper and lower bound for the target value(s).

The user interface 25 is configured to receive input from a clinician, such as regarding maximum limit(s) 100 and minimum limit(s) 98 for the target value(s), and to produce information to the clinician. For example, the user interface may produce an alert to the clinician, such as a visual alert on a digital display and/or an audio alert through speakers, if the respiratory drive or any of the calculated target values 52, 54, 56 are outside of a predetermined acceptable range. In various embodiments, the user interface 25 may include a mouse, a keyboard, a voice input device, a touch input device for receiving a gesture from a user, a motion input device for detecting non-touch gestures and other motions by a user, and other comparable input devices and associated processing elements capable of receiving input from a user, such as a clinician. Output devices such as a video display or graphical display can display an interface further associated with embodiments of the system and method as disclosed herein. Speakers, printers, haptic devices and other types of output devices may also be included in the user interface 25.

Both patient spontaneous action and ventilator pressure support contribute to the breath volume, e.g., tidal volume, but only the patient's contribution to the breath volume indicates the strength of the patient's respiratory drive. The portion of the breath volume attributable to the patient can be isolated from the ventilator contribution by using patient compliance, a relationship of changes in lung volume to lung pressure, instead of breath volume, as indicator for the respiratory drive. The ventilation monitor measures the breath volume independently, which includes both the patient's breath drive and the ventilator pressure support contribution. Spontaneous action causes negative pressure in the lungs suctioning in breathing gas, but the ventilation monitor pressure measurement can identify only the positive support pressure and the total amount of gas breathed in by the patient. Patient compliance can be determined by the following equation:

$$C = \frac{TV}{dP} = \frac{TV_{spont} + TV_{supp}}{P_{supp}}$$

The numerator in the patient compliance calculation is the sum of spontaneous tidal volume and ventilator-driven volume, whereas the denominator corresponds to the ventilator pressure support only. $TV_{spont}$ is the measured breath volume of patient spontaneous breath, $TV_{supp}$ is the ventilator pressure support contribution, and $P_{supp}$ is the ventilator support pressure. Accordingly, the patient compliance grows larger the stronger the un-measurable patient's spontaneous negative pressure drive comprises of the total $TV_{spont}$, i.e. the larger the patient's respiratory drive is the larger the patient compliance will be.

In one embodiment, the spontaneous breathing support module 21 identifies the target values, including the target CO2 52, target breath rate 54, and target compliance value 56, as filtered values based on respective measured values from the patient's respiration over time. For example, the target values 52, 54, 56 may be average values or low-pass filtered values of the measured values (such as via a first order low pass filter). For instance, the target values 52, 54, 56 may be determined based on a predetermined number of previous measured values or measured values taken over a predetermined time period. The time constant advantageously matches with the time constant of the patient CO2 concentration-related time constants, which is on the range of minutes, such as 2-5 minutes. These values stabilize long term to balance the respiratory center stimulus and response and the ventilator delivered support pressure. This also allows identifying changes in patient comfort, i.e., respiratory drive as a difference between instantaneous measured value and the respective target value.

The spontaneous breathing support module 21 is arranged to, depending on the measured patient values (e.g. patient CO2, patient breath rate 64, and breath volume 66), and their comparison with the respective target values 52, 54, 56, either increase or decrease the support pressure 68. The spontaneous breathing support module 21 may also move the target values 52, 54, 56 towards the measurement values by feeding the new measured values to the filters calculating the target values 52, 54, 56. In one embodiment, the spontaneous breathing support module 21 contains code that executes the following rules.

If current patient CO2 is greater than the target CO2:
  Where there is no sign of respiratory discomfort in the form of increased respiratory drive strength, this indicates that the target CO2 is too low and should be increased—i.e., the respiratory stimulus is weak despite that the current patient CO2 is larger than the target CO2. Thus, the target CO2 will be increased by the spontaneous breathing support module 21. Likewise, the target value(s) for the drive strength indicator(s) (i.e., the target breath rate and/or the target patient compliance) is reduced towards the current value, which is the patient's current comfort value.
  Where respiratory drive is strong, such as a breath rate and/or patient compliance above the respective target values, the support pressure is increased in order to ease the patient's respiratory discomfort. Increased pressure support is needed to lower the respiratory drive.
If current patient CO2 is less than the target CO2:
  Where respiratory drive is strong, such as a breath rate and/or patient compliance above the respective target values, the target CO2 is too high. Thus, the target CO2 is decreased. Additionally, the target value(s) for the drive strength indicator(s) (i.e., the target breath rate and/or the target patient compliance) is increased towards the respective current measured value(s) to find the balance between the stimulus and respiratory drive.
  Where respiratory drive is weak (e.g., below the respective target(s)), the support pressure is decreased to reach the targeted stimulation. Additionally, the drive strength target(s) (i.e., the target breath rate and/or the target patient compliance) is increased.

In certain embodiments the spontaneous breathing support module 21 may also set limits for some or all of the target values 52, 54, 56. For example, the system 1 may be configured to receive clinician-supplied minimum limit(s) 98 and maximum limit(s) 100 for one or more of the target CO2 52, the target breath rate 54, and the target compliance value 56. The maximum limit(s) 100 sets an upper bound for what value can be assigned to the respective target value 52, 54, 56, and minimum limit(s) 98 sets a lower bound for what value can be assigned to the respective target value 52, 54, 56. These extreme limits 98, 100 are needed to bring the clinician's knowledge of appropriate patient under-laying health status and medication related conditions in order to set safety and error bounds for the system 1 that account for the patient's unique physiology, condition, etc.

Figure 3:
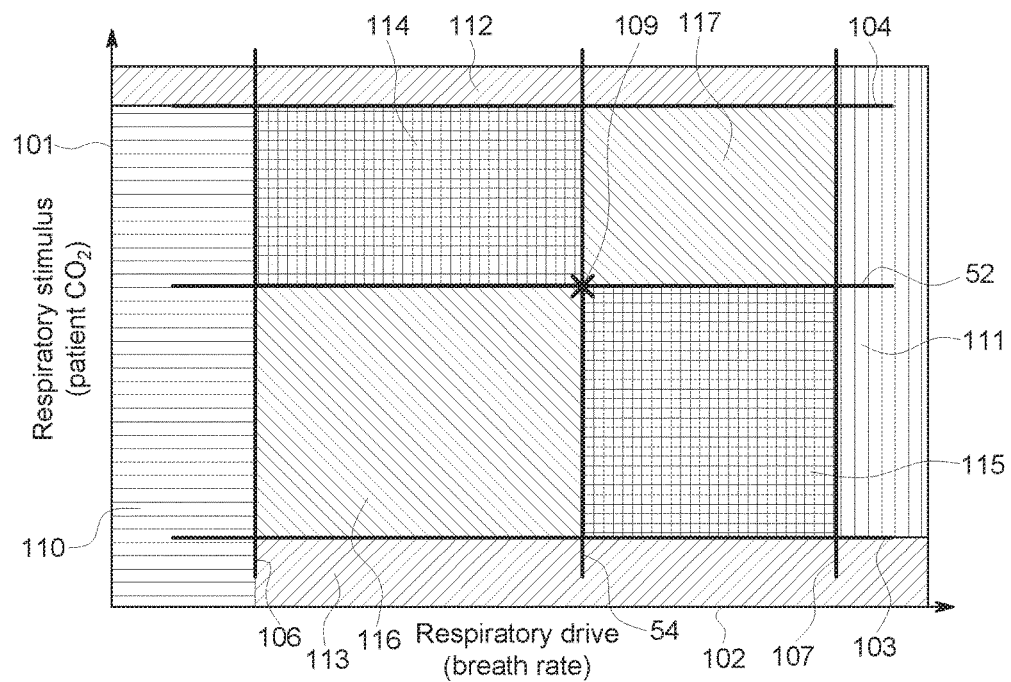
FIG. 3 is a graph depicting exemplary control operation of a spontaneous breathing support module.

FIG. 3 graphically represents an embodiment of a control strategy implemented by the spontaneous breathing support module 21 that incorporates clinician-set absolute limits 98 and 100 for each of the target values 52, 54, 56. The coordinate system represents respiratory center stimulus (patient CO2) on the vertical axis 101 and respiratory drive strength (e.g., breath rate) on the horizontal axis 102. In certain embodiments where only one respiratory drive strength variable is used, or a dominant respiratory drive strength variable is selected, breath rate 64 may be a preferred variable over patient compliance because patient response to increased respiratory stimulation with increased breath rate is more common than a response with increased breath volume. However, embodiments may also be desirable where breath volume (e.g. patient compliance) is the respiratory drive strength variable provided on the horizontal axis, which may be utilized alone or in combination with breath rate.

The coordinate area is divided by a minimum CO2 limit 103 and maximum CO2 limit 104 on the vertical axis 101, which provide lower and upper bounds for the respiratory center stimulation target, the target CO2 52. The coordinate area is also divided by a minimum breath rate limit 106 and maximum breath rate limit 107 on the horizontal axis 102, which provide lower and upper bounds for the respiratory drive strength target, the target breath rate 54. The targets 52 and 54 define the working target 109 for the support pressure 68 controlled by the spontaneous breathing support module 21.

The compliance changes can be conditionally included on the response at particular regions on the coordinate system. Control action provided by inputs, measured patient values, in the various regions 110-117 on the graph of FIG. 3 are presented in the following table. As described above, changes in the target values may be limited by the minimum limits 103, 106 and the maximum limits 104, 107 depicted in the table. In certain embodiments, minimum and maximum limits may also be set for patient compliance and/or target compliance value. In certain embodiments, a minimum limit for the patient compliance may be established based on a "normal state" for the patient, though it may be reduced further if the lung collapses over time. The minimum limit may set a floor, where the spontaneous breathing is not permitted to fall below the minimum limit for patient compliance. Accordingly, in such an embodiment, a decrease in patient compliance would only occur where the patient compliance was sufficiently above the minimum limit.

| Region | Patient compliance (or breath volume) | Target CO2 change | Target breath rate/volume change | Support pressure change | Rationale |
|---|---|---|---|---|---|
| 110 | Increasing | CO2 < Target CO2: decrease | decrease | none | Increased respiratory drive indicates patient discomfort above or below stimulation target. Decrease targets or increase support, respectively. |
|  |  | CO2 > Target CO2: none | none | Increase |  |
|  | Constant or decreasing | increase | decrease | decrease | Same or lower respiratory drive indicates weak patient stimulus. Decrease |

-continued

| Region | Patient compliance (or breath volume) | Target CO2 change | Target breath rate/volume change | Support pressure change | Rationale |
|---|---|---|---|---|---|
| 111 | N/A | decrease | increase | increase | support to increase stimulus. Patient breath rate above max limit, but CO2 above min limit. Add support to reduce strong patient stimulus. |
| 112 | N/A | decrease | move towards measured value | increase | Patient CO2 above max limit, but breath rate below max limit. Add support to reach target CO2 range. |
| 113 | N/A | increase | move towards measured value | decrease | Patient CO2 below min limit. Reduce support to reach target CO2 range. |
| 114 | Increasing | none | none | increase | Increased respiratory drive indicates patient discomfort. Increase support. |
| | Constant or decreasing | increase | decrease | none | Patient comfortable. Adjust targets. |
| 115 | Constant or increasing | decrease | increase | none | Patient comfortable. Adjust targets. |
| | Decreasing | none | none | decrease | Weak patient stimulus. Decrease support to increase stimulus. |
| 116 | Increasing | decrease | decrease | none | Patient comfortable. Adjust targets. |
| | Constant or decreasing | none | none | decrease | Weak patient stimulus. Decrease support. |
| 117 | N/A | none | none | increase | Increased respiratory drive indicates patient discomfort. Increase support. |

The target values, such as the target CO2 value 52 and the target breath rate 54, are adjusted as depicted, which may include based on the change or trend in the patient compliance. For example, the calculated patient compliance may be compared to a target compliance value 56. Alternatively, a trend in patient compliance may be determined, such as by determining a difference between the two most recently calculated compliance values or by calculating a derivative of a predetermined number of most recent patient compliance values.

If the measured point lands on a position where the target is not adjusted, no effect on the target occurs. If the measured point lands on a position where the target is adjusted, then the respective target(s) are increased or decreased as provided in the table. For example, the target CO2 value 52 and/or the target breath rate 54 may be adjusted by an amount equal to (patient value−target value)*gain. The gain may be a variable amount depending on the patient value. For example, the gain value applied to determine the target breath rate 54 may become smaller as the patient breath rate 64 increases. Since the control step is performed for each breath, this maintains a constant control speed over time because a higher breath rate adds to the number of control steps per unit time.

Figure 4:
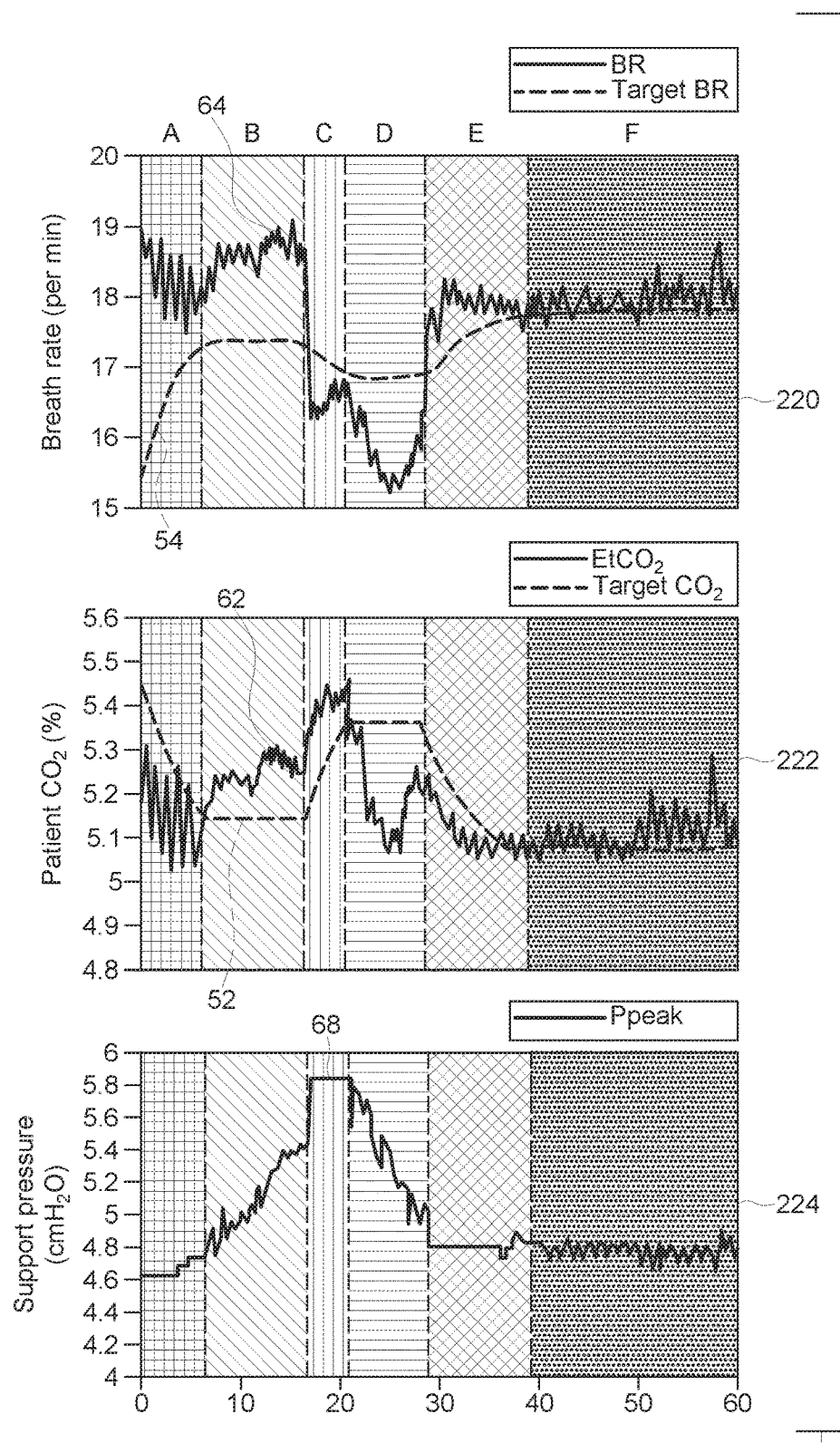
FIG. 4 provides graphs further exemplifying operation of the spontaneous breathing support module.

FIG. 4 provides a set of graphs exemplifying application of the rules and logic for spontaneous support ventilation represented in the forgoing table. The set of graphs present an exemplary scenario where breath rate (graph section 220), patient CO2 (graph section 222), and support pressure (graph section 224) interact over time according to control by the spontaneous breathing support module 21. The changing values in each region A-F on the graph are described below.

Region A: The measured patient CO2 52, the EtCO2, is below the target CO2 52, but the respiratory drive is still high as evidenced by the breath rate 64 being higher than the target breath rate 54. This means that the patient is aiming for a CO2 level below the current target CO2. Thus, the target CO2 52 is lowered. At the same time the target breathe rate 54 is increased. The goal is to find the values where the CO2-based activation and resulting breathe rate are in balance.

Region B: The measured patient CO2 52, the EtCO2, exceeds the target CO2 62, thus maintaining the patient's breathe rate 64 above the target breath rate 54. This indicates patient discomfort with the CO2 level, and so the support pressure 68 is increased Region C: The patient's breath rate 64 indicates comfort with the current patient CO2 level being above the target CO2. Thus, the target CO2 and target breath rate move towards the measured patient CO2 value and breath rate.

Region D: The low patient CO2 is dampening respiratory activity, as indicated by the low patient breathe rate 64. Thus, the support pressure is reduced to increase the respiratory drive.

Region E: The measured patient CO2 52, the EtCO2, is below the target CO2 52, but the respiratory drive is still high as evidenced by the breath rate 64 being higher than the target breath rate 54. So the target CO2 52 is reduced to be closer to the measured CO2 and the target breath rate 54 is increased to be closer to the measured breath rate 64 (similar to region A).

Region F: A stable state is reached where the patient's breathe rate 64 and ventilator support pressure 68 balance with the patient demand at the target CO2 52 level. Thus, the patient's breath rate 64 remains equal to the target breath rate 54 and the patient's CO2 62 remains equal to the target CO2 52.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. A method of controlling a ventilator to provide spontaneous breathing support, the method comprising:
   determining a target CO2 value;
   determining a support pressure;
   detecting a patient-generated spontaneous breath;
   delivering ventilation gas to the patient based on the support pressure;
   measuring a patient CO2;
   measuring at least one of a patient breath rate and a breath volume;
   comparing the patient CO2 to the target CO2 value;
   determining a difference between the patient CO2 and the target CO2 value;
   analyzing the at least one of the patient breath rate and the breath volume to assess a change in respiratory drive for the patient; and
   adjusting the target CO2 value based on the change in respiratory drive and the difference between the patient CO2 and the target CO2 value.

2. The method of claim 1, further comprising:
   detecting an elevated respiratory drive when the patient breath rate or the breath volume increase;
   adjusting the support pressure based on the patient CO2 and the at least one of the patient breath rate and the breath volume;
   detecting another patient-generated spontaneous breath; and
   delivering ventilation to the patient based on the adjusted support pressure.

3. The method of claim 1, wherein the target CO2 value is a defined based on patient CO2 measurement data.

4. The method of claim 3, wherein the target CO2 is defined based on an average of patient CO2 measurements during a predetermined previous time period.

5. The method of claim 3, further comprising:
   receiving at least one of a minimum limit and a maximum limit for the target CO2 value; and
   preventing the target CO2 value from decreasing below the minimum limit or exceeding the maximum limit.

6. The method of claim 1, further comprising:
   defining a target breath rate;
   measuring the patient breath rate;
   comparing the patient breath rate to the target breath rate; and
   adjusting at least one of the support pressure and the target CO2 value based further on the patient breath rate.

7. The method of claim 6, further comprising:
   determining that the patient CO2 is greater than the target CO2 value;
   increasing the support pressure if the patient breath rate is greater than the target breath rate; and
   decreasing the target CO2 value if the patient breath rate is less than or equal to the target breath rate.

8. The method of claim 6, further comprising:
   determining that the patient CO2 is less than the target CO2 value;
   increasing the target CO2 value if the patient breath rate is greater than the target breath rate; and
   decreasing the support pressure if the patient breath rate is below the target breath rate.

9. The method of claim 6, further comprising:
   measuring the breath volume of the patient;
   calculating a patient compliance based on the breath volume and the support pressure; and
   adjusting at least one of the support pressure and the target CO2 value based on the patient compliance.

10. The method of claim 9, further comprising:
    determining that the patient CO2 is less than the target CO2 value;
    decreasing the target CO2 value if the patient breath rate is greater than the target breath rate and the patent compliance is not decreasing;
    decreasing the support pressure if the patient breath rate is greater than the target breath rate and the patent compliance is decreasing;
    decreasing the target CO2 value if the patient breath rate is less than the target breath rate and the patent compliance is increasing; and
    decreasing the support pressure if the patient breath rate is less than the target breath rate and the patent compliance not increasing.

11. The method of claim 9, further comprising:
    determining that the patient CO2 is greater than the target CO2 value;
    increasing the support pressure if the patient breath rate is greater than the target breath rate;
    increasing the target CO2 value if the patient breath rate is less than the target breath rate and the patent compliance is not increasing; and
    increasing the support pressure if the patient breath rate is less than the target breath rate and the patent compliance is increasing.

12. The method of claim 6, wherein the target CO2 is a filtered value based on a predetermined amount of patient CO2 measurements and the target breath rate is a filtered value based on a predetermined amount of patient breath rate measurements, further comprising:
    receiving at least one of a minimum limit and a maximum limit for the target breath rate;
    preventing the target breath rate from decreasing below the minimum limit or exceeding the maximum limit;
    receiving at least one of a minimum limit and a maximum limit for the target CO2 value; and
    preventing the target CO2 value from decreasing below the minimum limit or exceeding the maximum limit.

13. The method of claim 12, further comprising:
    determining that the patient breath rate is above the maximum limit for the target breath rate and that the patient CO2 is above the minimum limit for the target CO2 value;
increasing the support pressure; and
providing an alert regarding elevated patient stimulus.

14. A ventilator system comprising:
a gas supply containing breathing gas;
a ventilator circuit that outputs the breathing gas from the gas supply to a patient and receives expiration gas from the patient;
a gas analyzer that measures a CO2 content in the expiration gas and determines a patient CO2;
a spontaneous breathing support control module is executable to:
define a target CO2 value for spontaneous breathing support ventilation;
define a support pressure for spontaneous breathing support ventilation;
detect a patient-generated spontaneous breath;
deliver a ventilation gas to the patient based on the support pressure;
receive a patient CO2 measured in expiration gas for the patient;
measure at least one of a patient breath rate and a breath volume;
compare the patient CO2 to the target CO2 value;
analyze the at least one of the patient breath rate and the breath volume to assess a change in respiratory drive for the patient; and
adjust the CO2 target value based on the change in respiratory drive and a difference between the patient CO2 and the target CO2 value.

15. The ventilator system of claim 14, wherein the control module is further configured to:
detect elevated respiratory drive when the patient breath rate or the breath volume exceed a threshold value;
adjust the support pressure based on the patient CO2 and the at least one of the patient breath rate and the breath volume;
detect another patient-generated spontaneous breath; and
deliver ventilation to the patient based on the adjusted support pressure.

16. The ventilator system of claim 14, wherein the target CO2 value is defined based on an average of the patient CO2 measurements over a predetermined previous time period.

17. The ventilator system of claim 16, wherein the control module is further configured to:
receive at least one of a minimum limit and a maximum limit for the target CO2 value; and
prevent the target CO2 value from decreasing below the minimum limit or exceeding the maximum limit.

18. The ventilator system of claim 14, wherein the control module is further configured to:
define a target breath rate;
measure the patient breath rate;
compare the patient breath rate to the target breath rate; and
adjust at least one of the support pressure and the target CO2 value based further on the patient breath rate.

19. The ventilator system of claim 18, wherein the control module is further configured to:
if the patient CO2 is greater than the target CO2 value, increase the support pressure when the patient breath rate is greater than the target breath rate and increase the target CO2 value when the patient breath rate is less than or equal to the target breath rate; and
if the patient CO2 is less than the target CO2 value, decrease the target CO2 value when the patient breath rate is greater than the target breath rate and decrease the support pressure when the patient breath rate is below the target breath rate.

20. The ventilator system of claim 14, wherein the control module is further configured to:
measure the breath volume of the patient;
calculate a patient compliance based on the breath volume and the support pressure;
determine a change in the patient compliance; and
adjust at least one of the support pressure and the target CO2 value based further on the change in patient compliance.

* * * * *